United States Patent

Leoni

[11] Patent Number: 5,772,681
[45] Date of Patent: Jun. 30, 1998

[54] DILATION CATHETER

[75] Inventor: Gianni Leoni, Greve, Denmark

[73] Assignee: Metra ApS, Greve, Denmark

[21] Appl. No.: 513,908

[22] PCT Filed: Mar. 2, 1994

[86] PCT No.: PCT/DK94/00086

§ 371 Date: Oct. 30, 1995

§ 102(e) Date: Oct. 30, 1995

[87] PCT Pub. No.: WO94/20166

PCT Pub. Date: Sep. 15, 1994

[30] Foreign Application Priority Data

Mar. 2, 1993 [DK] Denmark .................................. 0232/93

[51] Int. Cl.$^6$ .................................................. A61M 29/00
[52] U.S. Cl. ............................ 606/192; 606/194; 606/198
[58] Field of Search .................................... 606/194, 191,
606/192, 195, 198, 200; 604/96, 97, 98,
102, 103; 128/657

[56] References Cited

U.S. PATENT DOCUMENTS 5,328,469  7/1994  Coletti ...................................... 606/194
5,360,443  11/1994  Barone et al. ........................... 606/194

Primary Examiner—Michael Buiz
Assistant Examiner—Kevin Truong
Attorney, Agent, or Firm—Richard J. Godlewski

[57] ABSTRACT

A dilation catheter comprising a sealed distal end section (8), an open proximal end section (3) and an elongated middle section with an elongated flexible balloon section (11). The middle section comprises an inner elastic tube (1), a reinforcement net (2) made of metallic monofilaments surrounding the inner tube (1) and an outer elastic tube (6) surrounding the reinforcement net (2). The reinforcement net (2) is made of metallic monofilaments crossing each other and being helically wound around the longitudinal axis of the middle section. There is no special bond between the monofilaments so that said filaments are moveable with respect to each other in the crossover points (5) during expansion of the balloon section (11). As a result the entire catheter assumes the geometrical configuration of the blood vessel during insertion and inflation of the dilation section without noticeable axial dislocation or distortion of the natural bent of the blood vessel.

10 Claims, 2 Drawing Sheets

DILATION CATHETER

TECHNICAL FIELD

The present invention relates to a dilation catheter comprising a sealed distal end section, an open proximal end section and an elongated middle section, one part of said section being an elongated flexible balloon section expanding when supplied with pressure fluid through the proximal end section, said balloon section assuming a form of predominantly constant cross-section, said middle section comprising an inner elastic tube, a reinforcement net made of metallic monofilaments surrounding the inner tube and an outer elastic tube surrounding the reinforcement net, the parts of said middle section being situated outside the balloon section being predominantly unexpandable or expandable to a lesser degree than the balloon section, said reinforcement net is made of metallic monofilaments crossing each other and being helically wound around the longitudinal axis of the middle section, the helices being inside each other or braided, and said reinforcement net abuts on the outer surface of the inner tube and the inner surface of the outer tube at least in the area of the balloon section when the balloon section is expanded.

The invention also relates to a dilation catheter comprising a sealed distal end section, an open proximal end section and an elongated middle section, one part of said middle section being an elongated flexible balloon section expanding when supplied with pressure fluid through the proximal end section, said balloon section assuming a form of predominantly constant cross-section, said middle section comprising an inner elastic tube, a reinforcement net made of metallic monofilaments surrounding the inner tube and an outer elastic tube surrounding the reinforcement net, the parts of said middle section situated outside the balloon section being predominantly unexpandable or expandable to a lesser degree than the balloon section, said reinforcement net is a knitted net of metallic monofilaments, the mesh rows of said net extending helically around the longitudinal axis of the middle section, and said reinforcement net abuts on the outer surface of the inner tube and the inner surface of the outer tube at least in the area of the balloon section when the balloon section is expanded.

BACKGROUND ART

Radiologists, cardiologists and urologists have always preferred to perform dilation operations using systems assuming non-linear configurations when inflated. In the mid-sixties two well-known physicians, Judkins and Dottier, were the first to introduce a system for dilation of blood vessels using a coaxial double catheter system. This old technique was later modified by a famous physician who lent his name to the well-known Gruentzig balloon catheter to be used for coronary angioplasty, also known as PTCA (percutaneous transluminal coronary angioplasty). The various embodiments of balloon dilation catheters can be divided into two main classes. Balloons of one main class are normally not reinforced, i.e. not laminated. The balloon is sealed to an outer shaft having two lumens, one of which is used to inflate the balloon, the other as a guide-wire. Balloons of the second main class are coaxial constructions, i.e. they function according to a telescopic principle whereby fluid migrates between to layers directly connected to the balloon at the distal end.

The best known patent specification relating to a balloon dilation catheter of the first main class is U.S. Pat. No. 4,195,637 disclosing a balloon assuming a straight cylindrical configuration when expanded under pressure. This best known and probably most widely used system for dilation of blood vessels is not particularly flexible.

A second, less widely used dilation technique, as mentioned above, makes use of a coaxial system, having the detrimental effect that inflation of the balloon causes displacement of the catheter in the blood vessel. Also in this case a straight, cylindrical, inflexible balloon is formed, cf. U.S. Pat. No. 4,706,607 and DK-B154,870. A variation of a reinforced laminate structure for a balloon is disclosed in GB-B-1,566,674. This embodiment of a balloon dilation catheter functioning according to a telescopic principle is based on a compensation element during contraction of the balloon when the latter is exposed to internal pressure. This embodiment is not suitable for flexibility or bending during inflation.

A third design principle for a balloon dilation catheter especially used for PTCA is disclosed in EP-A1-0,388,486. This known balloon dilation catheter can be adjusted to various balloon diameters compared to the abovementioned ones, since the proximal end comprises a regulator allowing for axial mesh change in the balloon section. The last mentioned publication also disclosing metallic filaments to be used as reinforcement material for the balloon dilation catheter does not discuss in greater detail the possibilities of freely moveable contact points of the links in a laminate net structure under weak external pressure. This design is not suitable for flexibility or bending during inflation.

DISCLOSURE OF THE INVENTION

The object of the invention is to provide a dilation catheter with a flexible balloon section assuming the three-dimensional geometrical configuration of a blood vessel and permitting dilation of stenotic blood vessels or organs without distortion or dislocation thereof when the balloon section is inflated.

The dilation catheter according to the invention is characterized in that there is no special bond between the monofilaments so that said filaments are moveable with respect to each other in the crossover points during expansion of the balloon section.

In an alternative embodiment the dilation catheter according to the invention is characterized in that there is no special bond between the parts of the monofilament so that these parts are moveable with respect to each other in the crossover points during expansion of the balloon section.

The use of the laminate structure according to the invention—comprising a layer of inner tubing, the reinforcement net and a layer of outer tubing—for a dilation catheter is advantageous compared to other laminate structures for the same purpose, in which the section reinforced with normal plastic filaments (nylon, polyester etc.) forms a straight, cylindrical object when exposed to internal compressive stress, because a dilation catheter according to the invention permits permanent bending of said reinforcement net without permanent deformation of the metallic filaments. Manufactured from metallic monofilaments, helically wound, braided or knitted, the reinforcement net constituting the reinforced section of the laminate structure to resist internal pressure, may under very weak external influence assume various permanent three-dimensional configurations since the contact points of the reinforcement net are freely rotateable. The laminate structure thus deviates from the known straight, cylindrical balloon designs. The present invention comprises all possible geometrical three-dimensional configurations. Such three-dimensional configurations are formed by the bent artery or vein helping to fit the entire catheter in non-inflated condition, whereupon the expandable section, i.e. the balloon section, assumes its final external diameter by means of internal pressurizing following the natural curvature of the arterial configuration.

In principle such a design can be used for various purposes, its main object being to adapt to its surroundings. The invention allows dilation of a stenotic blood vessel or other inflicted parts of the body without axial distortion or three-dimensional dislocation as is the case with existing balloon catheters, reinforced or not.

According to the invention the metallic monofilament has an ultimate elongation at fracture of max. 5%.

The internal and external elastic tubes may according to the invention be advantageously made of thermoplastic materials.

The middle section of the dilation catheter according to the invention may comprise a non-expandable part of greater length than the balloon section.

Furthermore, the dilation catheter according to the invention may be provided with a guide-wire in its internal lumen.

DESCRIPTION OF THE DRAWINGS

The invention is described in greater detail below and with reference to the accompanying drawings in which.

PREFERRED EMBODIMENT OF THE INVENTION

Figure 1:
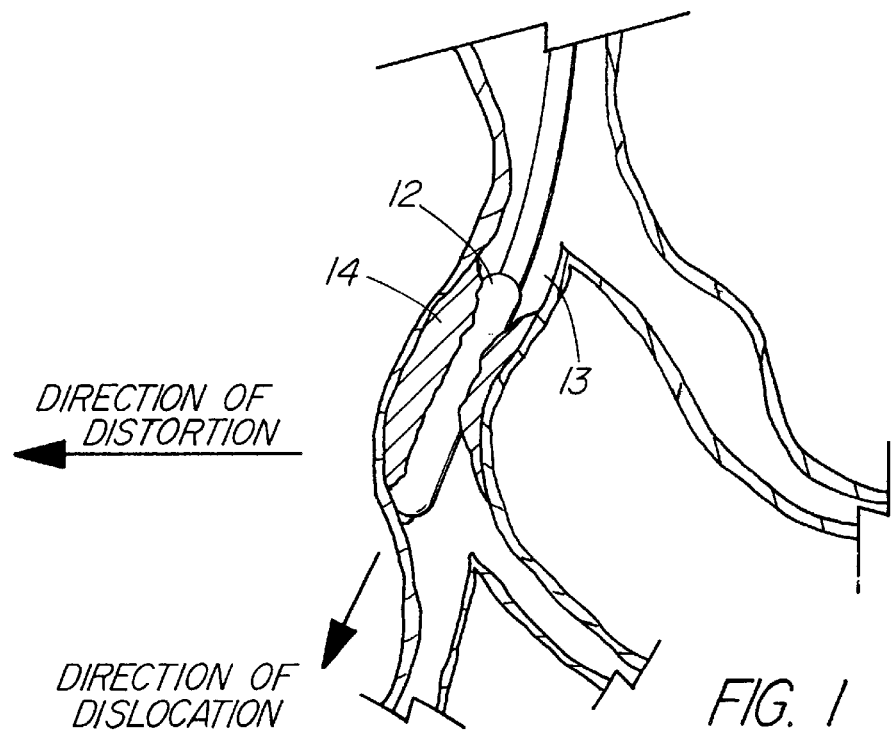
FIG. 1 is a longitudinal sectional view through a state-of-the-art dilation catheter with a balloon section inserted into a blood vessel.

FIG. 1 shows a state-of-the-art dilation catheter with a balloon section 12 inserted in a blood vessel 13 of a patient suffering from stenosis 14. The inflated balloon section 12 is dilationally engaged in the patient and has a straight cylindrical configuration. The direction of distortion indicated by one arrow and the direction of dislocation shown by an another arrow show that the blood vessel of the patient is at risk of rupturing.

Figure 2:
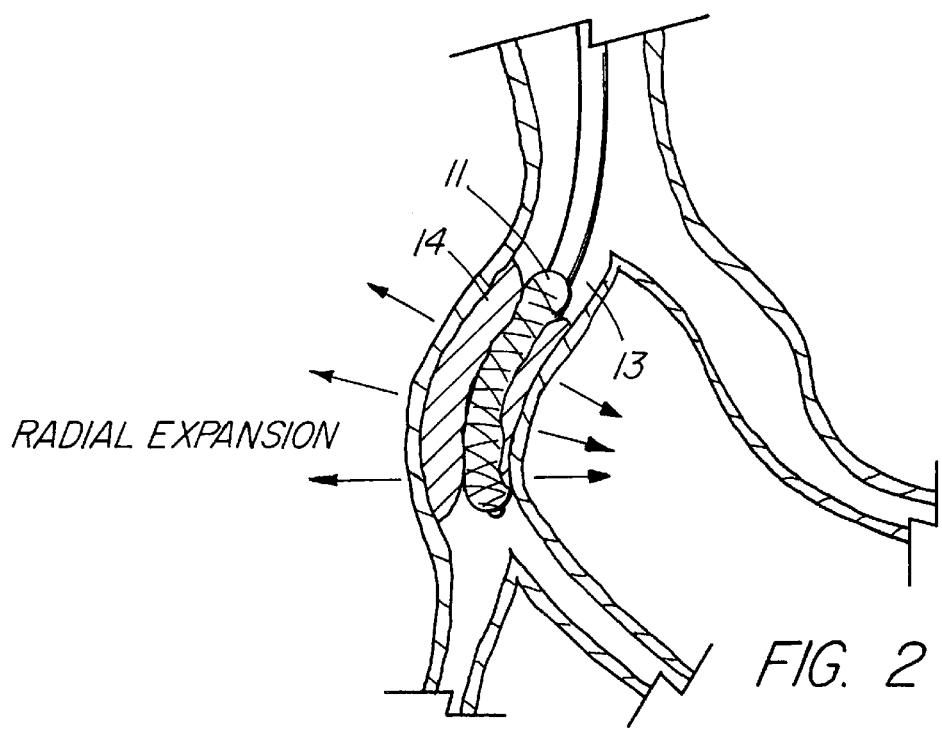
FIG. 2 is a longitudinal sectional view through an embodiment of a dilation catheter according to the invention inserted into the same blood vessel as in FIG. 1.
Figure 3:
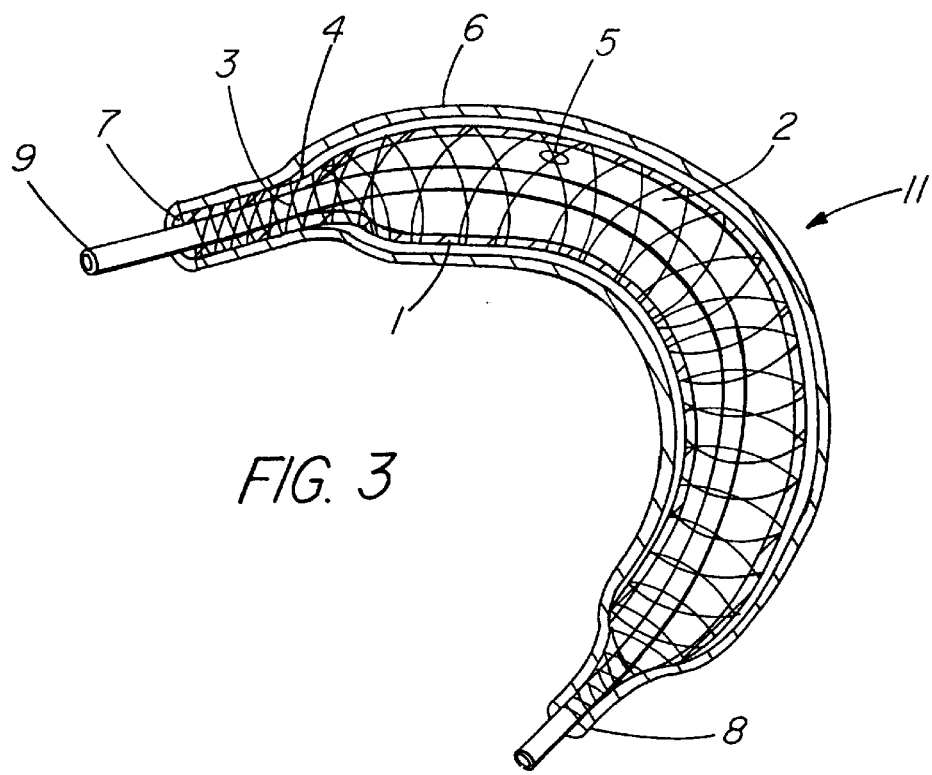
FIG. 3 is a longitudinal sectional view on a larger scale through the dilation catheter of FIG. 2 in bent position.

FIGS. 2 and 3 show a dilation catheter according to the invention.

The dilation catheter of FIG. 3 has a flexible balloon section 11 comprising an inner elastic tube 1 of polymeric material, said tube forming a chamber for fluid. Adjacent to the outer surface of the tube 1 a reinforcement net 2 of metallic monofilaments is provided, the mesh rows of said net extending helically around the longitudinal axis of the balloon section 11 thereby deviating from the neutral angle (54.7°). The contact points of the mesh rows are moveable with respect to each other in the crossover points 5 with and without internal pressure, i.e. during expansion of the balloon section. In continuation of the mesh row of the balloon section there is a longer section of mesh rows 3 at the neutral angle, a short transition piece 4 forming a continuous net between the catheter shaft and the balloon section 11. The distal end 8 is also provided with a continuous short transition piece from the mesh of the balloon section having a non-neutral angle to a section of mesh rows at the neutral angle. On top of the reinforcement net 2 there is an outer elastic tube 6 of polymeric material providing the outer part of the balloon section 11. The proximal end 7 of the balloon section 11 is provided with an opening for the passage of fluid. The internal space of the balloon section 11 comprises a pipe 9 staring at the connecting piece (not shown) of the dilation catheter and fastened to the distal end 8.

A flexible dilation catheter according to the invention is advantageously manufactured by using a cylindrical mandril made of metal or plastics, a thin elastic supporting layer 1 being either extruded or coated, the supporting layer forming the inner tube having a thickness of $5/100$–$10/100$ mm. The supporting layer 1 is then reinforced with metallic monofilaments with a diameter of 0.02–0.04 mm either helically wound, knitted or braided to form a reinforcement net 2, braiding being preferred. The reinforcement net 2 is then coated with an outer elastic layer 6 to form the outer tube (made of plastics or rubber) having a wall thickness of $5/100$–$10/100$ mm. The present invention makes use of thermoplastic polyurethanes for both inner and outer tube, vulcanized rubber being another suitable material. During coating of the elastic outer layer it is sought to avoid a chemical or mechanical bond between the contact points 5 of the reinforcement net 2. A thermoplastic material is generally considered the most approprioate for such a laminate structure, said thermoplastic material being preferred to vulcanized rubber. The laminate structure of the balloon and the shaft forming the dilation catheter is divided into three distinct sections. At each end of the expanding object, i.e. the balloon section 11, the reinforcement of the net is tighter 3, i.e. the number of monofilaments per unit length is larger than at the beginning 4 of the expandable section where the deviation from the neutral angle (54.7°) is smaller. The neutral angle of 54.7° is obtained by internal pressurizing, the two very short transition pieces of the balloon forming the collar of the balloon. Compared to a helical laminate the braided one is more stable and its degree of flexibility larger during identical external pressurizing.

Figure 4:
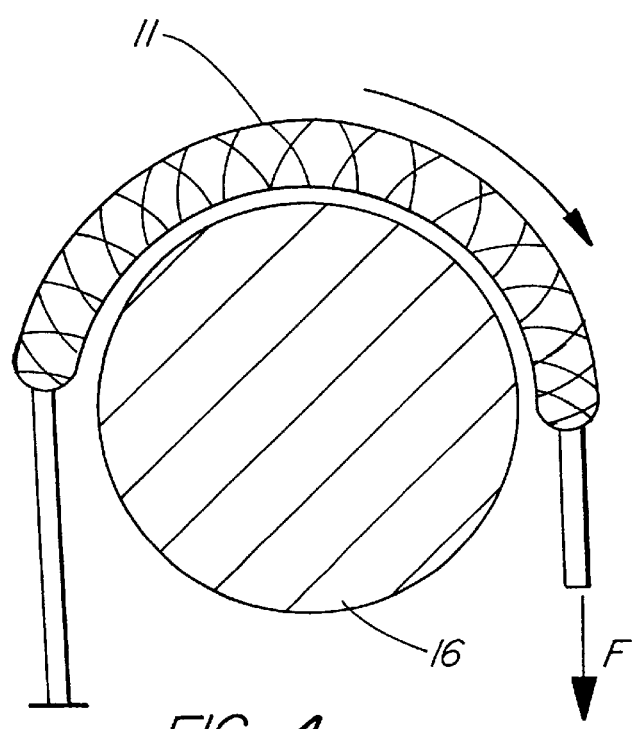
FIG. 4 is a schematic cross-sectional view through an apparatus for measuring flexibility.

FIG. 4 shows an apparatus for measuring flexibility. It is used to measure the flexibility of inflated balloons with and without reinforcement, said balloons having identical diameters and lengths and being exposed to identical pressure and temperature (37° C.). A catheter, the balloon section 11 of which is to be measured, is affixed as a "tangent" on a stainless steel cylindrical mandril 16 with a diameter of 18 mm. One side of the balloon 11 is retained while the other is bent around the mandril 16 by 180°. The vertical force F necessary for maintaining the 180° bending is measured by a calibrated spring dynamometer. The results are shown in table 1.

TABLE 1

| TYPE | BALLOON DIAMETER mm | PRESSURE MPa | FORCE N | STANDARD DEVIATION N |
|---|---|---|---|---|
| Reinforced with metallic filament | 2.70 | 1.2 | 0.12 | 0.03 |
| ditto | 1.30 | 0.0 | 0.07 | 0.01 |
| Reinforced with plastic filament | 2.70 | 1.2 | 1.43 | 0.21 |
| ditto | 1.35 | 0.0 | 0.67 | 0.14 |
| Not reinforced | 2.70 | 1.2 | NP | NP |

(NP = not possible)
The numbers are averages of 6 measurements.

The following table 2 shows the varying angle for a balloon reinforced with metallic monofilaments as a function of pressure. At zero pressure the balloon section is bent 90°, then the pressure rises.

TABLE 2

| PRESSURE MPa | 0.0 | 0.2 | 0.5 | 0.7 | 1.0 | 1.3 | 1.7 | 1.9 |
|---|---|---|---|---|---|---|---|---|
| ANGLE | 90 | 90 | 90 | 90 | 90 | 93 | 95 | 97 |
| BALLOON DIAMETER, mm | 1.3 | 1.4 | 1.7 | 2.3 | 2.7 | 2.7 | 2.7 | 2.7 |

It was not possible to perform similar measurements with a dilation catheter reinforced with plastic filaments (nylon), since the balloon section at zero pressure was a straight cylinder and could not be deformed with a constant angle but returned always to 180°. The same applied to the non-reinforced balloon dilation catheter.

An important aspect of the present invention with respect to laminate balloons reinforced with metallic filaments, especially with a braided mesh, is that when the balloon is exposed to a weak external force, e.g. when it has to pass through a bend, the balloon retains the bent form even when exposed to internal pressure, i.e. it expands. An important advantage of the balloon according to the invention compared to balloons reinforced with plastic filaments or non-reinforced balloons is that the latter types have a straight cylindrical configuration carrying the risk of dislocation of the blood vessels during inflation, cf. FIG. 1.

At suitable material for the metallic monofilament for the reinforcement net are metal alloys such as NiTi.

The dilation catheter according to the invention may for example be exposed to a maximum pressure of 25 bar.

I claim:

1. A dilation catheter comprising a sealed distal end section (8), an open proximal end section (3) and an elongated middle section, one part of said middle section being an elongated flexible balloon section (11) expanding when supplied with pressure fluid through the proximal end section (3), said balloon section assuming a form of predominantly constant cross-section, said middle section comprising an inner elastic tube (1), a reinforcement net (2) made of metallic monofilaments surrounding the inner tube (1) and an outer elastic tube (6) surrounding the reinforcement net (2), wherein said reinforcement net (2) is made of metallic monofilaments crossing each other and being helically wound around the longitudinal axis of the middle section, the helices being and braided, wherein said reinforcement net (2) abuts on the outer surface of the inner tube (1) and the inner surface of the outer tube (6) at least in the area of the balloon section (11) when the balloon section (11) is expanded, and wherein said filaments are moveable with respect to each other in the crossover points (5) during expansion of the balloon section (11).

2. A dilation catheter according to claim 1, wherein said metallic monofilament has an ultimate elongation of 5%.

3. A dilation catheter according to claim 1, wherein the inner (1) and outer elastic tubes (6) are made of thermoplastic material.

4. A dilation catheter according to claim 1, wherein the middle section also comprises a non-expandable part having a greater length than the balloon section (11).

5. A dilation catheter according to claim 1, wherein a guide-wire is provided in an inner lumen of said dilation cather.

6. A dilation catheter comprising a sealed distal end section (8), an open proximal end section (3) and an elongated middle section, one part of said middle section being an elongated flexible balloon section (11) expanding when supplied with pressure fluid through the proximal end section (3), said balloon section assuming a form of predominantly constant cross-section, said middle section comprising an inner elastic tube (1), a reinforcement net (2) made of metallic monofilaments surrounding the inner tube (1) and an outer elastic tube (6) surrounding the reinforcement net (2), wherein said reinforcement net (2) is a knitted net of metallic monofilaments, mesh rows of said net extending helically around the longitudinal axis of the middle section, wherein said reinforcement net (2) abuts on the outer surface of the inner tube (1) and the inner surface of the outer tube (6) at least in the area of the balloon section (11) when the balloon section (11) is expanded, and wherein said mesh rows are moveable with respect to each other in the crossover points (5) during expansion of the balloon section.

7. A dilation catheter according to claim 6, wherein said metallic monofilament has an ultimate elongation of 5%.

8. A dilation catheter according to claim 6, wherein the inner (1) and outer elastic tubes (6) are made of thermoplastic material.

9. A dilation catheter according to claim 6, wherein the middle section also comprises a non-expandable part having a greater length than the balloon section (11).

10. A dilation catheter according to claim 6, wherein a guide-wire is provided in an inner lumen of said dilation catheter.

* * * * *